US012778229B1

(12) United States Patent
Dobbs

(10) Patent No.: US 12,778,229 B1
(45) Date of Patent: Nov. 3, 2026

(54) EYELASH EXTENSION AFTERCARE SYSTEM AND METHODS

(71) Applicant: Cherie L. Dobbs, Winter Garden, FL (US)

(72) Inventor: Cherie L. Dobbs, Winter Garden, FL (US)

( * ) Notice: Subject to any disclaimer, the term of this patent is extended or adjusted under 35 U.S.C. 154(b) by 20 days.

(21) Appl. No.: 18/535,645

(22) Filed: Dec. 11, 2023

Related U.S. Application Data

(62) Division of application No. 16/875,797, filed on May 15, 2020, now Pat. No. 11,839,252.

(60) Provisional application No. 62/849,793, filed on May 17, 2019.

(51) Int. Cl.

| | |
|---|---|
| ***A41G 5/02*** | (2006.01) |
| ***A45D 34/04*** | (2006.01) |
| ***A61K 8/43*** | (2006.01) |
| ***A61K 8/9789*** | (2017.01) |
| ***A61K 8/9794*** | (2017.01) |
| ***A61Q 90/00*** | (2009.01) |

(52) U.S. Cl.
CPC ............. *A41G 5/02* (2013.01); *A45D 34/042* (2013.01); *A61K 8/43* (2013.01); *A61K 8/9789* (2017.08); *A61K 8/9794* (2017.08); *A61Q 90/00* (2013.01); *A45D 2200/10* (2013.01); *A61K 2800/87* (2013.01)

(58) Field of Classification Search
CPC ...... A41G 5/02; A61K 8/9794; A61K 8/9789; A61K 8/43; A61K 2800/87; A45D 34/042; A45D 2200/10; A61Q 90/00
See application file for complete search history.

(56) References Cited

U.S. PATENT DOCUMENTS

| | | | | |
|---|---|---|---|---|
| 10,278,915 | B1 * | 5/2019 | Kawa | A61K 8/345 |
| 2003/0153486 | A1 * | 8/2003 | Storet | A61K 8/37 512/25 |
| 2011/0300083 | A1 | 12/2011 | Yontz et al. | |
| 2017/0112739 | A1 * | 4/2017 | Molenda | A61K 8/19 |
| 2017/0347731 | A1 | 12/2017 | Chipman et al. | |
| 2020/0078287 | A1 * | 3/2020 | Fischer | A61K 47/32 |
| 2021/0401730 | A1 * | 12/2021 | Laperdrix | A61Q 7/00 |

FOREIGN PATENT DOCUMENTS

| | | | | |
|---|---|---|---|---|
| WO | WO-2018157974 A1 * | 9/2018 | | A61K 8/466 |
| WO | WO-2018162834 A1 * | 9/2018 | | A61K 36/88 |

* cited by examiner

*Primary Examiner* — Doan T Phan

(74) *Attorney, Agent, or Firm* — Stout, Uxa & Buyan, LLP; Donald E. Stout

(57) ABSTRACT

A convenient after care cleanser and application method for eyelash extensions allows for easy application, extension of the longevity of the lashes, elimination of protein build-up that eventually accumulates on the lashes, and other benefits.

4 Claims, 2 Drawing Sheets

EYELASH EXTENSION AFTERCARE SYSTEM AND METHODS

This application is a divisional application under 35 U.S.C. 120 of U.S. application Ser. No. 16/875,797, entitled Eyelash Extension Aftercare System and Methods, filed on May 15, 2020 and issued as U.S. Pat. No. 11,839,252 on Dec. 12, 2023, which in turn claims the benefit under 35 U.S.C. 119(e) of the filing date of Provisional U.S. Application Ser. No. 62/849,793, entitled Eyelash Extension Aftercare System and Methods, filed on May 17, 2019. Both of these prior applications are expressly incorporated herein by reference, in their entirety.

BACKGROUND OF THE INVENTION

Existing approaches for cleaning eyelash extensions are both inadequate and dauntingly complicated for the average consumer. As a result, such extensions often are not properly cleaned. Natural oils and dead skin cells, when not washed away properly, can build up on the eyelids, and can cause itchiness and inflammation. In some cases, eye infections can result.

SUMMARY OF THE INVENTION

The present invention addresses the problems discussed above by finally providing a safe, convenient, and effective after care for professional eyelash extensions.

There is provided, in one aspect of the present invention, an eyelash extension cleaning system, comprising a container having an interior volume, an open end, and a closed end. A brush applicator wand is removably disposed in the interior volume of the container, and comprises a base on a first end thereof, a brush on a second end thereof, and a wand connecting the base and the brush. An eyelash extension cleanser is disposed in the interior volume, so that the brush is in contact with the cleanser when the brush applicator wand is disposed in the interior volume. The base of the brush applicator wand is engageable with the open end of the container, such as by a threaded connection, to secure the brush applicator wand to the container for storage and transport.

The eyelash extension cleanser comprises a blend of blue agave juice, hops extract, and cotton extract. In some blends, the eyelash extension cleanser further comprises Indian cress extract. More particularly, in one particular exemplary formulation, the eyelash extension cleanser comprises a blend of water, azul agave tequilana leaf extract juice, glycerin, *gossypium herbaceum* (cotton) seed extract, gluconolactone, polyaminopropyl biguanide, triglycerides, nettle extract, decyl glucoside, horse chestnut extract, *arnica* extract, Indian cress extract, lauryl glucoside, *Humulus lupulus* (hops) extract, and *leuconostoc*/radish root ferment filtrate. The triglycerides, in an exemplary embodiment, comprise capric/caprylic triglycerides.

In another aspect of the invention, there is provided a cleanser for application to eyelash extensions, comprising a blend of blue agave juice, hops extract, and cotton extract. In some formulations, the eyelash extension cleanser blend further comprises Indian cress extract. In one particular formulation, the eyelash extension cleanser comprises a blend of water, azul agave tequilana leaf extract juice, glycerin, *gossypium herbaceum* (cotton) seed extract, gluconolactone, polyaminopropyl biguanide, triglycerides, nettle extract, decyl glucoside, horse chestnut extract, *arnica* extract, Indian cress extract, lauryl glucoside, *Humulus lupulus* (hops) extract, and *leuconostoc*/radish root ferment filtrate.

In still another aspect of the invention, there is disclosed a method of providing after care for eyelash extensions. The method comprises removing a brush applicator wand from a container having a supply of eyelash extension cleanser therein, the bush applicator wand comprising a base on a first end, a brush on a second end, and a wand joining the base to the brush, the removing step being performed by grasping the base, disengaging the base from the container, and pulling the brush application out of the container, wherein the brush retains some of the supply of eyelash extension cleanser thereon. The, the brush applicator wand is moved to contact eyelash extensions to be cleaned with the brush, after which the brush applicator is moved to move the brush along the eyelash extensions, to thereby deposit the cleanser onto the eyelash extensions.

The cleanser, in exemplary embodiments, comprises a blend of blue agave juice, hops extract, and cotton extract. In some formulations, the cleanser further comprises Indian cress extract. In a particular formulation, the cleanser comprises a blend of water, azul agave tequilana leaf extract juice, glycerin, *gossypium herbaceum* (cotton) seed extract, gluconolactone, polyaminopropyl biguanide, triglycerides, nettle extract, decyl glucoside, horse chestnut extract, *arnica* extract, Indian cress extract, lauryl glucoside, *Humulus lupulus* (hops) extract, and *leuconostoc*/radish root ferment filtrate.

The invention, together with additional features and advantages thereof, may best be understood by reference to the following description taken in conjunction with the accompanying illustrative drawing.

DETAILED DESCRIPTION OF THE INVENTION

Figure 1:
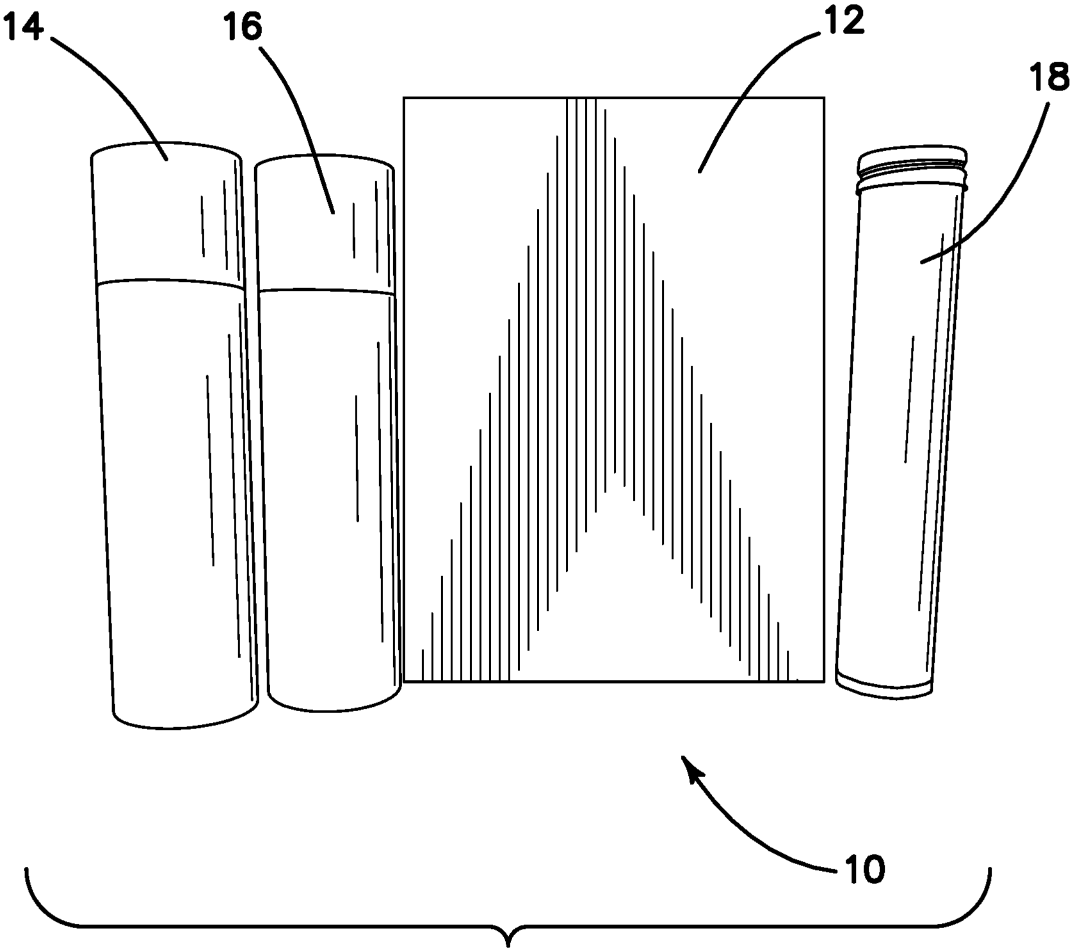
FIG. 1 is a view of an eyelash extension care kit formulated and assembled in accordance with the principles of the present invention.
Figure 2:
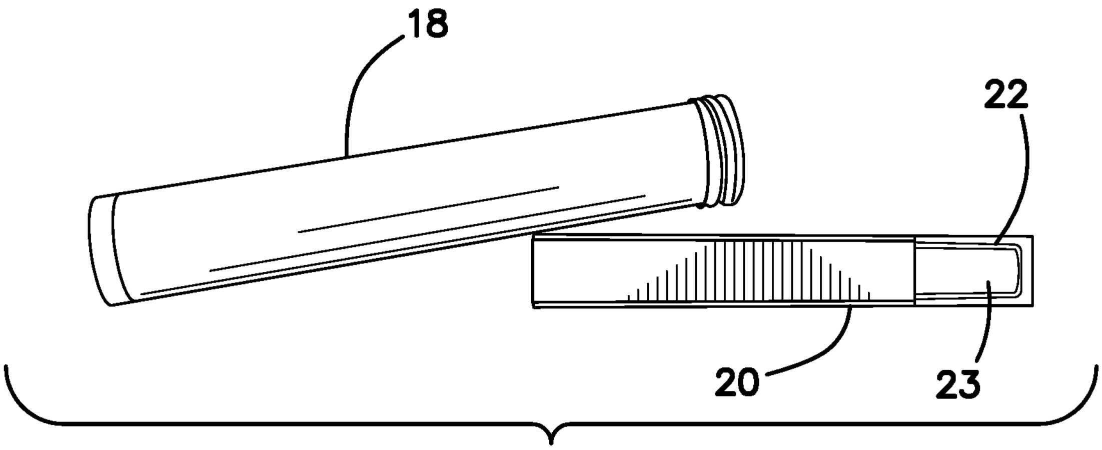
FIG. 2 is a view of the canister shown in FIG. 1, which has been opened and its contents, comprising a container for a brush applicator, removed therefrom.
Figure 3:
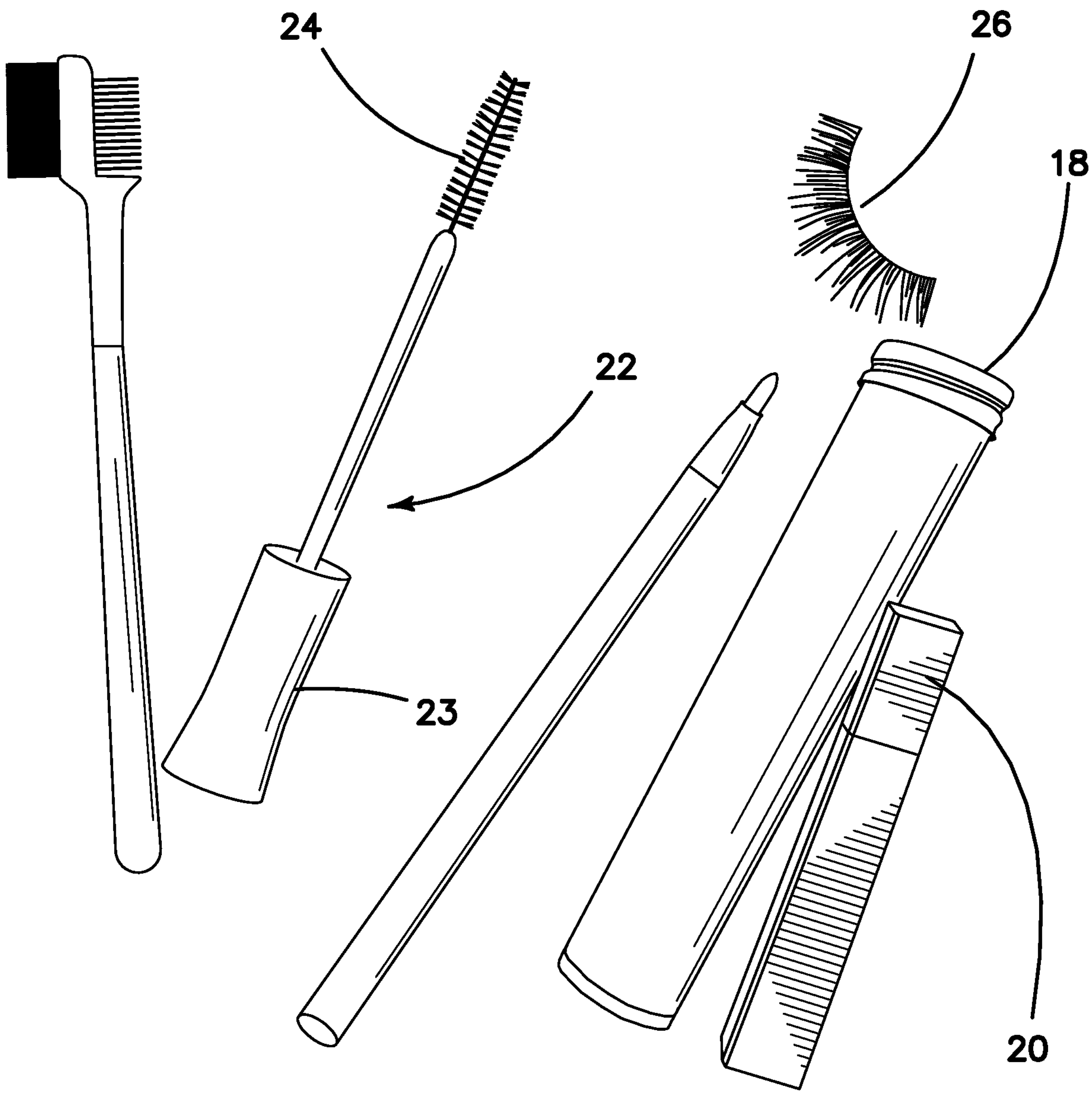
FIG. 3 is a view of the kit of FIG. 1 in a disassembled form.

The present invention comprises, in one exemplary embodiment, a kit 10 as shown in FIG. 1. The kit may comprise a box 12, for holding some or all of the kit elements, a container 14 of eyelash clean and conditioning cleanser, a container 16 of faux lash cleanser, and a canister 18, which accommodates a container 20, as shown in FIG. 2. The container 20, in turn, holds a quantity of lash cleanser, as well as a brush applicator wand 22 (FIG. 3), having a brush 24 at a distal end thereof. The container 20 is similar to a mascara application system (mascara wand tube) in many respects.

The inventive system helps to prevent dirty lashes, is convenient and easy to use, extends lash fills, cleanses the area from sweat and bacteria, fluffs the lashes, and prevents caked tangle lashes. It is a convenient, healthy way to extend the longevity of the user's lashes and helps to eliminate protein build-up that eventually accumulates on the lashes, causing caked-looking lashes. Using the system daily helps to clean, fluff, untangle, and protect the integrity of the lashes. The inventive cleanser includes a natural anti-bacterial agent against pathogens. A hops extract included in the cleanser is also loaded with nutrient-rich amino acids which nourish the skin. The cleanser is oil-free, alcohol-free, will not deteriorate lash glue, will not compromise lash integrity, kills sebaceous bacteria, does not strip natural skin oils, and will not dry out surrounding skin.

In operation, a user removes the container 20 from the canister 18 and opens the container 20 on one end, removing the brush applicator wand 22 from the container 20 by pulling on base 23 of the applicator 22. Since the brush 24 is disposed in a supply of cleanser stored in the container 20, some of the cleanser will be retained on the brush 24 as the applicator wand 22 is removed from the container 20.

Holding the applicator in the hand, by the base 23, the user gently spools or twirls the brush 24 on the lashes 26 to be cleaned. Though shown separately, it is both safe and preferred to clean the lashes 26 while adhered in place on the user's regular eyelashes, as the cleanser will not deteriorate the lash glue or be harmful in any way. After application, the lashes may be splashed with warm water and patted dry. Use in the morning will help untangle and straighten overlapping lashes from side sleeping positions.

The cleanser stored in the container 20 is a blend of active ingredients, which include blue agave juice, hops extract, and cotton extract. The blue agave juice is included because agave saponins not only promote cleansing action but, due to their structure, allow the penetration of moisturizing active ingredients in hair. Agave's sugars lock moisture inside the hair, building strength, resiliency, and elasticity.

The hops extract is a natural anti-bacterial agent against pathogens, and are also loaded with nutrient-rich amino acids which nourish the skin. The cotton extract has been found by the inventor to be particularly beneficial because carbohydrates and proteins contained in the seeds act as a moisturizing and conditioning agent for the skin and protect the hair against external aggressions, thus increasing its elasticity and helping to repair and condition the hair.

Another ingredient which is preferably included in the cleanser is Indian cress extract. The sulphurated derivatives have rubefacient properties, stimulating micro-circulation and thus helping with oxygen proliferation and bringing organic Sulphur as a constituent to the hair bulb. The fatty acids prevent the development of bacteria in the pilo-sebaceous sacs and in the sebaceous gland, minimizing oil build-up.

In one particular formulation, the ingredients of the inventive lash cleanser include water, azul agave tequilana leaf extract juice, glycerin, *gossypium herbaceum* (cotton) seed extract, gluconolactone, polyaminopropyl biguanide, triglycerides (capric/caprylic triglycerides), nettle extract, decyl glucoside, horse chestnut extract, *arnica* extract, Indian cress extract, lauryl glucoside, *Humulus lupulus* (hops) extract, and *leuconostoc*/radish root ferment filtrate.

Accordingly, although an exemplary embodiment of the invention has been shown and described, it is to be understood that all the terms used herein are descriptive rather than limiting, and that many changes, modifications, and substitutions may be made by one having ordinary skill in the art without departing from the spirit and scope of the invention.

What is claimed is:

1. An eyelash extension cleanser blend for application to eyelash extensions, comprising blue agave juice, hops extract, cotton extract, Indian cress extract, water, glycerin, gluconolactone, polyaminopropyl biguanide, triglycerides, nettle extract, decyl glucoside, horse chestnut extract, *arnica* extract, lauryl glucoside, and *leuconostoc*/radish root ferment filtrate.

2. A method of providing after care for eyelash extensions, the method comprising:

removing a brush applicator wand from a container having a supply of eyelash extension cleanser blend therein, the bush brush applicator wand comprising a base on a first end, a brush on a second end, and a wand joining the base to the brush, the removing step being performed by grasping the base, disengaging the base from the container, and pulling the brush application out of the container, wherein the brush retains some of the supply of eyelash extension cleanser blend thereon;

moving the brush applicator wand to contact eyelash extensions to be cleaned with the brush; and moving the brush applicator to move the brush along the eyelash extensions, to thereby deposit the eyelash extension cleanser blend onto the eyelash extensions, wherein the eyelash extension cleanser blend comprises blue agave juice, hops extract, cotton extract, Indian cress extract, water, glycerin, gluconolactone, polyaminopropyl biguanide, triglycerides, nettle extract, decyl glucoside, horse chestnut extract, *arnica* extract, lauryl glucoside, and *leuconostoc*/radish root ferment filtrate.

3. The eyelash extension cleanser blend as recited in claim 1, wherein the blue agave juice is azul agave tequilana leaf extract juice.

4. The eyelash extension cleanser blend as recited in claim 1, wherein the cotton extract is *gossypium herbaceum* (cotton) seed extract.

* * * * *